(12) United States Patent
Reime (10) Patent No.: US 9,404,728 B2
(45) Date of Patent: Aug. 2, 2016

(54) SENSOR FOR LOCATING METAL OBJECTS AND ASSOCIATED COIL

(76) Inventor: Gerd Reime, Buhl (DE)

( * ) Notice: Subject to any disclaimer, the term of this patent is extended or adjusted under 35 U.S.C. 154(b) by 46 days.

(21) Appl. No.: 14/237,945

(22) PCT Filed: Aug. 3, 2012

(86) PCT No.: PCT/EP2012/003323
§ 371 (c)(1),
(2), (4) Date: Feb. 10, 2014

(87) PCT Pub. No.: WO2013/020686
PCT Pub. Date: Feb. 14, 2013

(65) Prior Publication Data
US 2014/0191750 A1    Jul. 10, 2014

(30) Foreign Application Priority Data

Aug. 10, 2011  (DE) .......................... 10 2011 109 870
Jan. 24, 2012  (DE) .......................... 10 2012 001 202

(51) Int. Cl.
*G01N 27/72*   (2006.01)
*G01B 7/14*    (2006.01)
*G01V 3/10*    (2006.01)

(52) U.S. Cl.
CPC *G01B 7/14* (2013.01); *G01N 27/72* (2013.01); *G01V 3/107* (2013.01)

(58) Field of Classification Search
CPC ........... G01B 7/14; G01V 3/107; G01N 27/72
USPC .................................................. 324/239, 240
See application file for complete search history.

(56) References Cited

U.S. PATENT DOCUMENTS

| | | | |
|---|---|---|---|
| 2,867,783 A * | 1/1959 | Childs | 336/123 |
| 4,096,463 A * | 6/1978 | Gitzendanner et al. | 336/129 |
| 4,255,711 A | 3/1981 | Thompson | |
| 5,804,963 A | 9/1998 | Meyer | |
| 5,966,011 A * | 10/1999 | Goldfine et al. | 324/242 |
| 6,144,206 A | 11/2000 | Goldfine et al. | |
| 8,570,028 B2 * | 10/2013 | Ely | 324/207.15 |
| 2010/0181995 A1 | 7/2010 | Inoue | |

FOREIGN PATENT DOCUMENTS

| | | |
|---|---|---|
| DE | 3619308 C1 | 8/1991 |
| DE | 4339419 C2 | 5/1995 |

(Continued)

OTHER PUBLICATIONS

International Search Report for corresponding application PCT/EP2012/003323 filed Aug. 3, 2012; Mail date Jun. 6, 2013.

*Primary Examiner* — Reena Aurora
(74) *Attorney, Agent, or Firm* — Cantor Colburn LLP (57) ABSTRACT

A sensor for locating metal objects has coils or coil parts which form at least one transmitting coil (5.1) and at least one receiving coil (7.1) which are inductively coupled to one another and are arranged such that said coils partially overlap for the purpose of interaction decoupling, wherein optimum cancellation of the interaction can be achieved. Sensor electronics are provided for energizing the transmitting coil and for evaluating a reception signal (10.6) from the receiving coil. As a result of the fact that the transmitting coil (5.1) and the receiving coil (7.1) substantially have an identical coil shape and are arranged such that said coils are rotated and/or offset with respect to one another, wherein a plurality of symmetrically arranged, overlapping regions (8.4) are formed, a sensor which provides a greater range and extended possibilities for installation in conventional industrial sensor housings is provided.

9 Claims, 7 Drawing Sheets

(56) References Cited

FOREIGN PATENT DOCUMENTS

| | | |
|---|---|---|
| DE | 19738841 A1 | 3/1999 |
| DE | 10301951 A9 | 10/2004 |
| DE | 10318350 B3 | 12/2004 |
| DE | 102004047188 A1 | 3/2006 |
| DE | 102004047189 A1 | 4/2006 |
| DE | 102010005399 A1 | 8/2010 |
| DE | 102009042940 A1 | 5/2011 |
| WO | 02091021 A1 | 11/2002 |
| WO | 2010084000 A1 | 7/2010 |
| WO | 2010133328 A1 | 11/2010 |

* cited by examiner

SENSOR FOR LOCATING METAL OBJECTS AND ASSOCIATED COIL

CROSS REFERENCE TO RELATED APPLICATIONS

The present invention claims priority from German patent applications 10 2011 109 870.8, filed on 10 Aug. 2011, and 10 2012 001 202.0, filed on 24 Jan. 2012, the entire contents of which are herein incorporated by reference.

FIELD OF THE INVENTION

The invention relates to a sensor for locating metal objects and to an associated coil.

BACKGROUND

Metal detectors operate by various principles. In some constructions, only one coil is used, and this is for example part of an oscillator. As metal is approached, the voltage at the oscillation circuit of the oscillator changes. This change in voltage is then analyzed accordingly and used to determine the metal.

Other measurement principles use a coil to emit an electromagnetic pulse which generates an eddy current in the metal part that is to be detected. This eddy current is typically received by a second coil and analyzed accordingly.

According to another method, a transmitting coil is used to emit a continuous alternating field which is received by a second coil. In relation to the first coil (transmitting coil), this second coil is arranged such that, in the absence of an effect by the metal in an object to be detected, the magnetic effect of the transmitting coil is eliminated in the receiving coil. The mechanical arrangement of the transmitting and the receiving coil must be selected to be very stable, since any small displacement or deformation will immediately give rise to an output signal in the receiving coil.

In a further method disclosed in WO 2010/084000 A1 and WO 2010/133328 A1, use two transmitting coils, which are offset from one another, and continually—that is, whether or not a metal is present—regulate a receiving signal to zero with the current components. In this system, temperatures that affect the receiving coil and the preamplifier have no effect on the measured detected value. The detected value is derived from the ratio of regulated transmitted currents, with the result that, even if the transmitted currents are almost the same, the possibility that temperature affecting the coil arrangements will affect the detected value may be ruled out. Mechanical deformations of the coil arrangements merely result in an offset in the detected value, since the receiving signal remains at zero.

In the methods last mentioned above, a coil arrangement is used in which the magnetic field or fields of the transmitting coil or coils is/are eliminated in the receiving coil or coils. Only the component originating in the metal object to be detected is measured. For this purpose, the coils are arranged to overlap such that the emitted magnetic field is eliminated in the receiving coil in the absence of an effect from metal. The coils only overlap with one another over a small part of the coil surface. This part is the most sensitive region for the purpose of detection. However, the majority of the coil surfaces does not overlap, so this gives large coil systems having only a small sensitive region, which is typically also asymmetrical in relation to the overall coil system.

Figure 1:
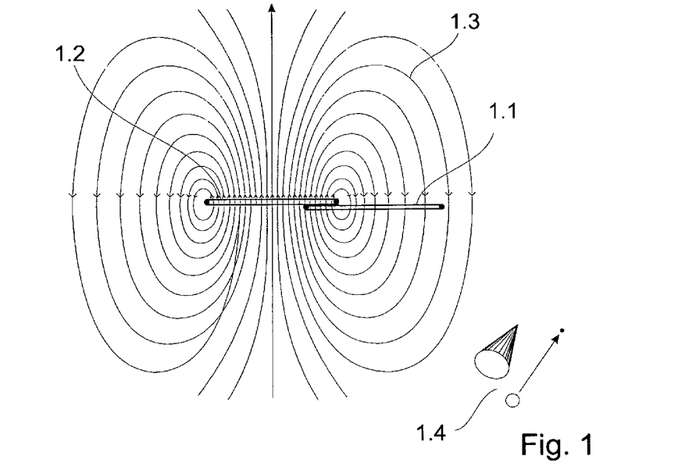
FIG. 1 shows an illustration of the magnetic field lines of a transmitting coil.

In the case of so-called "treasure hunting" or "mine detector" devices, such as those known from DE 43 39 419 C2, a coil arrangement is frequently used in a double D arrangement. The transmitting coil and the receiving coil are mounted partly above one another in such a way that the coefficient of mutual inductance is minimal. The coils are operated alternately as transmitting and receiving coil. In this case, the two Ds are arranged with mirror symmetry and overlapping. It is clear from FIG. 1 why only a small part of the coils may overlap. This shows a coil arrangement from the side. The field lines 1.3 emanating from a transmitting coil 1.2 are more concentrated in the center point of the coil than in the external region surrounding the coil. The arrangement in FIG. 1 is the necessary result of the fact that the same number of field lines has to pass through the receiving coil 1.1 in the internal and the external region of the transmitting coil.

A metal detector operated in pulse induction (PI) mode is known from DE 103 01 951 A9. The interaction between the primary and secondary coils is decoupled by the partial overlap of the coplanar coil systems. The decoupling is adjusted by means of mechanically displaceable masses in the region of overlap, or by electrical compensation aids, for example in the form of additional compensation signals from the generator to the receiving circuit. These compensate for the proportion of the energy transmitted to the receiving coil that is not fully decoupled. There is no "feedback" between the signal detected by the receiving coil and the compensation effect—that is, there is no closed loop.

DE 103 18 350 B3 discloses a comparable arrangement in which a plurality of coils are nested within one another such that they are offset adjacent to one another and their alternating magnetic fields overlap. The largest coil, preferably the receiving coil, determines the periphery of the coil arrangement.

From DE 36 19 308 C1 is the converse of the principle mentioned above, that is to say that a surrounding transmitting coil has two figure-of-eight shaped receiving coils, which mutually cancel their emitted field.

From DE 10 2010 005 399 A1 is known the use of mutually rotatable meanders and coils in a position sensor, or to be more precise a crank angle sensor that measures the angle of the crank shaft on a vehicle motor. The meandering, as explained in paragraph (0029), is such that the coil forms a "meandering zigzag coil pattern" that meanders in a rectangular shape. This creates rectangular portions each protruding towards the outer periphery of the regulating circuit board and having connecting portions which connect respectively adjacent rectangular portions. If the coils are rotated in relation to one another at the speed of the crank shaft of the vehicle motor, a periodic oscillation is produced which can be detected in the various constructions to enable precise control of the motor. This produces a relatively high induced electrical output, but this is used only to simplify the rotary encoder.

DE 10 2004 047 189 A1 relates to a bar sensor or stud finder which is intended for example to locate metal objects hidden in building materials. These may be reinforcing bars or conductors and pipes hidden behind a wall. In order to reduce the offset problems of the prior art that occur as a result of the coil tolerances that are otherwise usual, conductor loop systems are constructed in the form of conductor structures on a circuit board. The transmitting coils and compensation and receiving conductor loops are arranged at a height offset to one another on the circuit boards.

DE 10 2004 047 188 A1, which also refers to a stud finder, aims to change the effective number of windings of a receiving winding system by using switching means to increase the sensitivity by alternative means. The solution is extremely similar in its construction to DE 10 2004 047 189 A1.

DE 10 2009 042 940 A1 relates to a position measuring device which, in accordance with FIGS. 3, 4, operates with meandering conductor tracks. The conductor tracks of a first group of serpentine conductor tracks and the conductor tracks of a second group of serpentine conductor tracks are connected to one another electrically conductively by way of a through-hole. As a result, crossing positions of the mutually crossing transmitter conductor tracks are produced and so there is no overlapping of a transmitter coil with a receiving coil.

WO 02/091021 A1 attempts, in the case of a stud finder, to achieve as small as possible an offset signal by inductive coupling of the transmitting coil and the receiving coil and, in a concentric arrangement, by dimensioning them in respect of the number of their windings and their sizes, or dimensioning the transmitting currents in respect of phasing and amplitude, such that mutual compensation takes place. In other words, the intention is to ensure that as far as possible no signal is produced unless an object comes close, with the result that an unambiguous signal is given when an object is located.

DE 197 38 841 A1 discloses periodic meandering triangular structures in an inductive angle sensor in order to bring about a detectable change when the angle changes.

U.S. Pat. No. 5,804,963 A1 discloses the basic principle of using meandering structures in order, in the case of a position sensor, to introduce periodically changing electromagnetic changes which help to make changes in a position sensor measurable. However, the meanders are only provided in certain parts and are not intended to increase the range by way of the said refinement of the measuring variables.

The fact that the term "field lines" should not be taken literally is known to all those skilled in the art, since to a certain extent they merely illustrate more easily regions of the same magnetic strength and polarity. For this reason, in the description of the invention that follows, this term will be used to indicate magnetic density. Coils are illustrated with only one winding, for the sake of better illustration. It will be readily appreciated that the invention takes as its starting point coils having a plurality of windings, or coils "printed" on a board. An alternating signal is operational in the coils; the field lines are indicated during a single clock phase.

BRIEF SUMMARY

Taking as a starting point this prior art, the invention provides a sensor for locating metal objects and a coil, each of which provides a greater range for the sensor or more options for installation in conventional industrial sensor housings.

The fact that the sensor has a coil system or a coil results in an improved range for metal detectors or proximity sensors, in that the size of the overlap regions between transmitting coil(s) and receiving coil(s) and hence also the sensitivity of detection is significantly increased with, at the same time, rotationally symmetrical detection properties. The region of sensitivity is almost rotationally symmetrical while having a low sensitivity at the outer edge, and has no near-field errors. Here, the term "coil system having rotationally symmetrical detection properties" is understood to mean a coil system in which almost congruent curves of the output voltage that occurs here are produced, regardless of the direction in which a metal object is guided over the coil system at a constant spacing. Thus, the coil system senses the object in almost the same way, whatever direction it comes from. For this purpose, preferably meandering loop portions of the windings of the transmitting and the receiving coil are formed. Here, the term "meandering loop portions" of a conductor forming a winding of a coil is understood to mean that a conductor that moves to and fro, preferably with the same width, along its longitudinal direction—in other words, meanders—takes the form of a coil, that is to say that the meander is curved in the manner of a coil, so to speak. As a result, the loop portions of a winding of the coil are then preferably formed such that the loop portions are made from preferably circular portions which are arranged to have differing radial spacings from the center point of a preferably circular coil, and are connected alternately to one another, preferably by way of radially arranged portions, to form an electrical conductor. As a result, there are produced portions of the meander-shaped winding of the coil which are open or closed alternately in the direction of the center point of the coil or outwardly, which results in the desired increase in the overlap regions.

For the purpose of decoupling the interaction, the transmitting and the receiving coil may be rotated and/or offset in relation to one another, preferably such that field lines of a field that is inverted in relation to the field lines caused by the supply of current to the transmitting coil are formed within the inwardly open loop portions of the receiving coil that meander along the periphery of the coil, while a field that acts in the same direction as the field lines of the transmitting coil and thus supports the action of the transmitting coil and increases the range is formed in the interior of the receiving coil.

BRIEF DESCRIPTION OF THE FIGURES

The invention will be explained in more detail below with reference to exemplary embodiments illustrated in the Figures, in which.

DETAILED DESCRIPTION OF PREFERRED EXEMPLARY EMBODIMENTS

The invention will now be explained in more detail and by way of example, with reference to the attached drawings. However, the exemplary embodiments are only examples, which are not intended to restrict the inventive concept to a particular arrangement. Before the invention is described in detail it should be pointed out that it is not restricted to the respective components of the device and the respective method steps, since these components and methods may vary. The terms used here are only intended to describe particular embodiments and are not used restrictively. Moreover, where the singular or indefinite articles are used in the description or the claims, this also refers to a plurality of these elements unless the overall context unambiguously indicates otherwise.

For the illustration of the field lines that is used below, 1.4 in FIG. 1 shows in symbolic form the direction of field lines in a plan view of the coil system. Thus, dots symbolize field lines running towards the observer, while circles represent the field lines running away from the observer.

Figure 2:
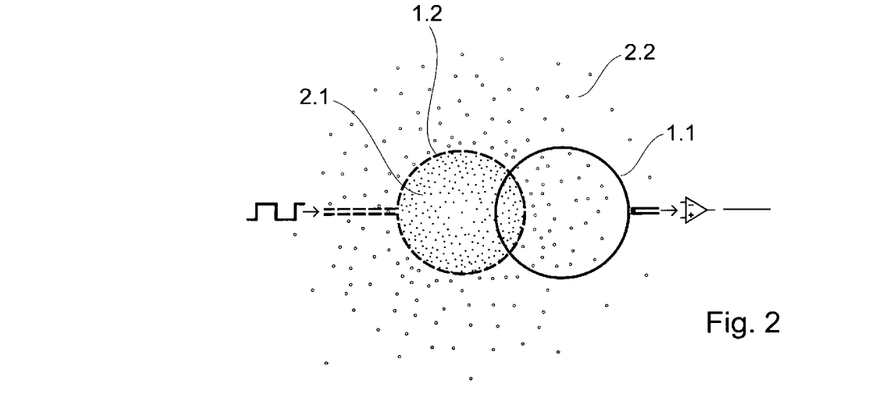
FIG. 2 shows a plan view of the coil system according to FIG. 1.

FIG. 1 shows, from the side, a known coil arrangement with overlapping transmitting coil 1.2 and receiving coil 1.1. Field lines 1.3 emanating from the transmitting coil 1.2 are more concentrated in the center point of the coil than in the external region surrounding the coil. The arrangement in FIG. 1 is the necessary result of the fact that the same number of field lines has to pass through the receiving coil 1.1 in the internal and the external region of the transmitting coil for the purpose of decoupling interaction. FIG. 2 shows the action of the known coil system according to FIG. 1, in which the transmitting coil 1.2 emits a field. The field lines 2.1 running towards the observer are concentrated within the transmitting coil 1.2, and the field lines 2.2 running away are distributed in a relatively large region around the coil. In order to achieve a zero signal with the receiving coil 1.1, it has to be arranged such that approximately the same number of "dot" field lines as "circle" field lines pass through the coil. In this way, the effect of the magnetic field in the coil is eliminated, and only the magnetic fields that are excited by the transmitting coil 1.2 and which emanate from the object to be detected are received. This is most effective in the region in which the coils overlap.

Figure 3:
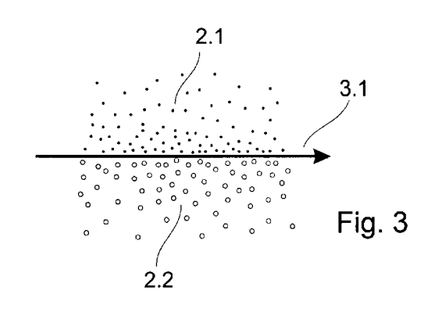
FIG. 3 shows the field lines around a straight conductor through which current flows.
Figure 4:
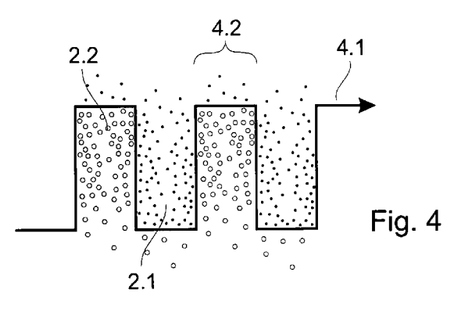
FIG. 4 shows the field lines around a meander-shaped conductor through which current flows.

In order to significantly increase the effectiveness of a coil system, the following approach was taken as the starting point: according to FIG. 3, a straight conductor 3.1 through which current flows forms field lines around it whereof the number decreases with distance from the conductor. By contrast, FIG. 4 shows the field lines around a meander-shaped conductor 4.1 through which current flows. The field lines are chiefly concentrated within the "coil portions" 4.2, which each comprise a half winding of the meander.

Figure 5:
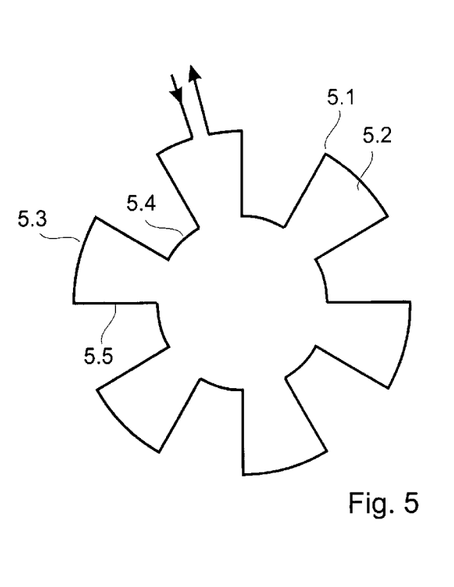
FIG. 5 shows a winding of a meander-shaped transmitting coil according to the invention.

In order to utilize this effect in a coil having multiple windings, the meander-shaped conductor is brought into a coil shape, that is to say that the meander is curved in the manner of a coil, so to speak. In FIG. 5, of this only one meander-shaped winding of the coil, a transmitting coil 5.1, is illustrated, with the receiving coil 7.1 according to FIG. 7 having a substantially identical coil shape.

Figure 7:
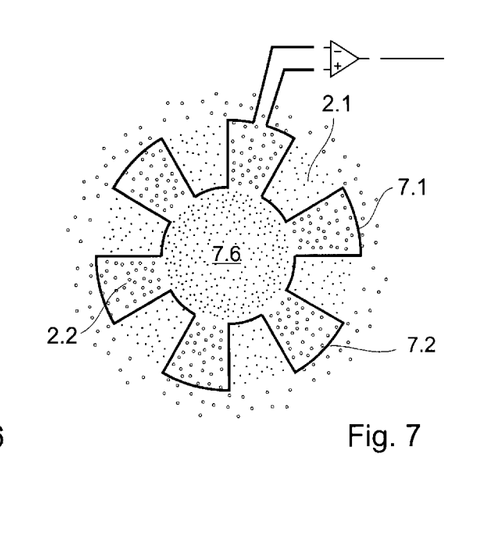
FIG. 7 shows the receiving coil with the associated field lines.

These coils are used to form a sensor for locating metal objects that has coils or coil parts that form at least one transmitting coil 5.1 and at least one receiving coil 7.1 which are inductively coupled to one another and are arranged to partly overlap for the purpose of decoupling interaction, wherein optimum cancellation of the interaction may be achieved.

A sensor electronics unit is provided for supplying current to the transmitting coil and for analyzing a receiving signal 10.6 from the receiving coil. According to FIG. 8, the transmitting coil 5.1 and the receiving coil 7.1 are rotated and/or offset in relation to one another, wherein a plurality of symmetrically arranged overlap regions 8.4 are formed. These overlap regions 8.4 are preferably arranged to have point symmetry in relation to the center point of the coils.

According to FIGS. 5 and 7, the coil shape has meandering loop portions 5.2, 7.2 arranged along the periphery of the planar coil or coil parts. The preferably circular coil has n loop portions 5.2, 7.2, where n is for example ≥6, wherein the loop portions of the transmitting coil 5.1 and the receiving coil 7.1 are arranged rotated about an angle of approximately 360°/(n*2). This means that where n=6 an angle of rotation of approximately 360°/(6*2)≈30°, which corresponds approximately to the angle bisector of the 60° angle of the respective loop portion when there are six loop portions. It will be explained below why the value is only approximately 30°.

The loop portions 5.2, 7.2 are composed of preferably circular portions 5.3, 5.4 which are arranged at a differing radial spacing from the center point of the circular coil and are connected to one another alternately, by way of preferably radially arranged portions 5.5, to form an electrical conductor. As a result, there are produced portions of the meander-shaped winding of the coil which are open or closed alternately in the direction of the center point of the coil or outwardly. Shapes other than circular or radially arranged portions are conceivable. For example, the portions 5.3, 5.4 may also be straight, or the portions 5.5 may not run radially in relation to the center. The crucial point is the formation of the loop portions 5.2, 7.2.

Figure 6:
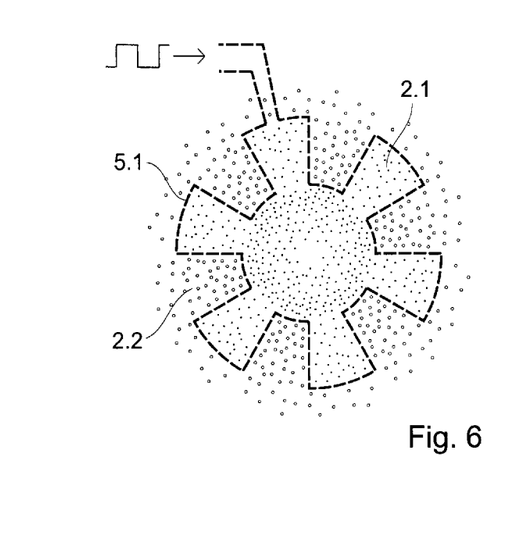
FIG. 6 shows the field lines of the transmitting coil that are produced in this case.

FIG. 6 shows the associated field lines of the transmitting coil 5.1 that are produced when a current flows through this coil. To distinguish them from the receiving coils, the transmitting coil(s) will be shown in each case in dashed lines in the illustrations of the invention below.

The meanders or loop portions 5.2, 7.2 may have any number n, this being a function of the coil embodiment used. The higher the number, the more rotationally symmetrical the behavior of the coil will be. In practice, a number of six to ten meandering loop portions on the circular periphery as illustrated in FIG. 5, for example for a printed coil, has been shown to be generally sufficient. The description below is given on the basis of a coil having six loop portions.

The receiving coil 7.1 may be composed in substantially the same way as the transmitting coil 5.1. It is mounted congruently on (or below) the transmitting coil, with an offset of "approximately" 30 degrees. As a result, it "receives" the same number of field lines in the other direction, such that the transmitting coil has no inductive effect on the receiving coil. A metal object that is in front of this coil system is excited by the transmitting coil 5.1, while the receiving coil regions, which at the center point are largely congruent, receive the field emitted by the metal object without disruption. Within the inwardly open loop portions 7.2 of the receiving coil 7.1 there are produced field lines of a field which is inverted in relation to the field lines caused by the supply of current to the transmitting coil, while there is formed in the interior 7.6 of the receiving coil a field which runs in the same direction as the field lines of the transmitting coil and supports the functioning and hence range of the transmitting coil.

Figure 8:
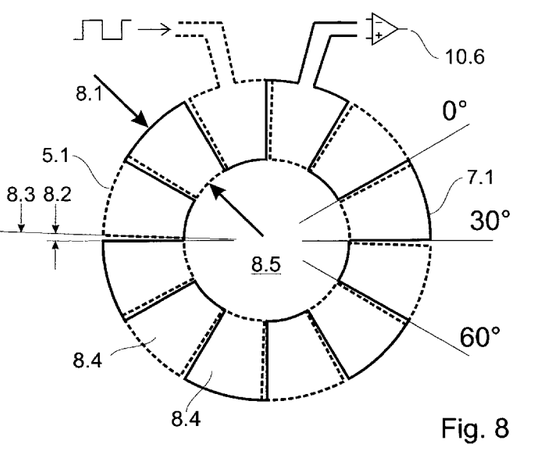
FIG. 8 shows a coil system with transmitting coil and receiving coil.

FIG. 8 shows a coil system having the transmitting coil 5.1 and the receiving coil 7.1. Both coils have an angle offset of almost 30°.

In the "double D" prior art, the inductive action of the transmitting coil on the receiving coil is cancelled as a result of displacing the coils in relation to one another. According to the invention, by contrast, the adjustment required for this cancellation is usually only performed when the coil system is calibrated, by changing the depth 8.1 of the meander, that is to say by changing the radial spacing of the portions 5.3, 5.4 or, if the depth is fixed, by rotating the coil angle 8.3 between the transmitting coil 5.1 and the receiving coil 7.1.

Figure 9:
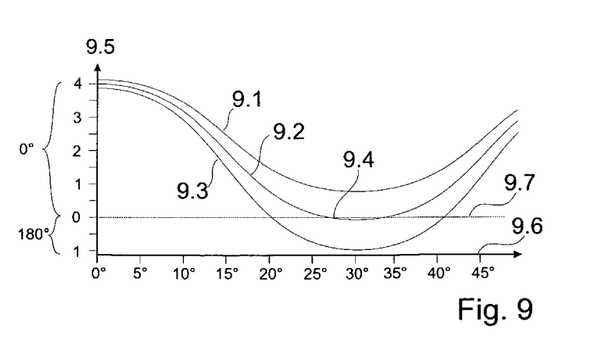
FIG. 9 shows the voltage at the receiving coil that is produced in the event of rotation in relation to the transmitting coil, with clocked transmitting current in the transmitting coil, over the angle of rotation.

FIG. 9 shows the voltage 9.5 that is produced at the receiving coil on rotation, with a clocked transmission current in the transmitting coil 5.1. (The values of the voltage are only example values.) Starting at 0 degrees, only the field lines 2.1 that are produced in the interior region of the transmitting coil 5.1 are detected. With a rotation of 30 degrees, the inverted external field lines 2.2 are additionally detected, while detection of the field lines 2.1 decreases accordingly. The coils are in an optimum arrangement when, at precisely 30° or already in a small angular region 8.2 before a 30° offset between the transmitting and the receiving coil is reached, the transmitting signal is cancelled in the receiving coil 7.1, that is to say that a value of zero is produced. The curve 9.2 that is associated with this can be seen to fall below the zero value at the position 9.4, that is to say a small angular region 8.2 (FIG. 8) before 30° is reached. The position of the transmitting coil that is associated with this is designated 8.3. We will come back to this below. In the position corresponding to the line of the curve 9.4, the magnetic fields of the transmitting coil 5.1 are therefore completely cancelled in the receiving coil 7.1. The size of the angular region 8.2 may be determined by the radial depth 8.1 (FIG. 8) of the meandering loop portions 5.2, 7.2.

If the depth 8.1 of the meandering loop portions is too small, on rotation about the angular value 9.6 the voltage decreases, until it reaches a minimum at 30 degrees before rising again. This is indicated by the curve 9.1. However, at the minimum of 30 degrees cancellation has not yet been achieved. This means that the loop portions are too small. If the depth of the meandering loop portions is too large, by contrast, the transmitting signal will bring about cancellation in the receiving coil 7.1 significantly before 30 degrees is reached. Then, continued rotation generates an inverted signal which has its maximum at an angular offset of 30°. This means that the loop portions are too large. A coil system of this kind may still be used in practice, but in this case the "overlap region" that is used jointly by both coils—or the effective surface area of transmission and reception—is reduced.

In this arrangement with coil angles 8.3 adjusted in fixed manner, mechanical effects such as deformation of the coil system, or indeed the influence of a metal, may result in displacement of the point 9.4 of optimum cancellation.

For this reason, in WO 2010/084000 A1 and WO 2010/133328 A1 it was proposed that two transmitting coils and respectively regulated coil currents be used in order to obtain a perfect zero signal. The description of the invention below refers to the above-mentioned patent applications. For the present invention, it is in particular crucial that, as a result of the interaction between the transmitting coils and at least one receiving coil, a local point of optimum cancellation of the fields emitted by the transmitting coils is produced in the receiving coils. In this case, the coils are arranged such that if the transmitting coil parts are supplied with equal current they have an effect on the at least one receiving coil by which a local point of optimum cancellation of the emitted fields is produced in the receiving coils. However, this point is displaced or moved in a first direction if a first transmitting coil, or a first part of the transmitting coil, is chiefly or solely supplied with current, while it is displaced or moved in a further direction, preferably in opposition to the first direction, if a further transmitting coil, or a further part of the transmitting coil, is chiefly or solely supplied with current. This local point of optimum cancellation is affected by the approach to a metal. A control circuit for regulating the currents of the transmitting coil parts results, in the event of regulation, in displacement of the local point of optimum cancellation, bringing about cancellation of the receiving signal. The control value required for this, and the change thereto, are preferably used as a measure of an approach to a metal or the locating of metal objects.

Figure 10:
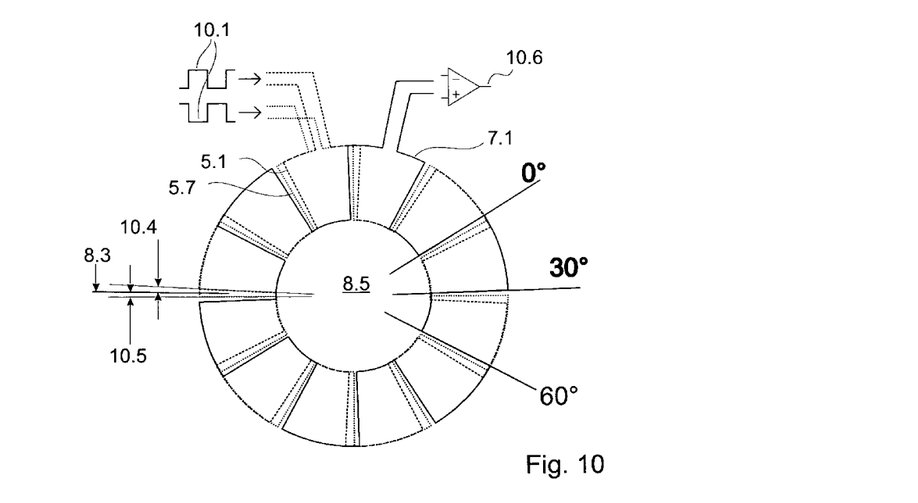
FIG. 10 shows a coil arrangement in a further exemplary embodiment according to the invention, having two transmitting coils which differ by a small angular extent.

In order to use two regulated transmitting currents for canceling the receiving signal in the receiving coil, two transmitting coils 5.1 and 5.7 which differ in their angle by a small extent and have regulated coil currents are used. FIG. 10 shows a coil arrangement of this kind. The transmitting coil 5.1 has a small angular offset 10.4 in the direction "upstream" of the coil angle 8.3 of optimum cancellation in an individual coil, and the further transmitting coil 5.7 has a small angular offset 10.5 "downstream" of the angle of optimum cancellation. The angular offsets may in practice be smaller than that illustrated in FIG. 10, being for example in the region of 0.2 degrees.

The coils are polarized such that the field lines in each clock phase 10.1 run in the same direction. If the current is the same in both transmitting coils 5.1 and 5.7, the effect of both transmitting coils together is equal to the effect of the individual coil in the exemplary embodiment of FIG. 5. Therefore, the transmitted magnetic fields are cancelled in the receiving coil.

Figure 11:
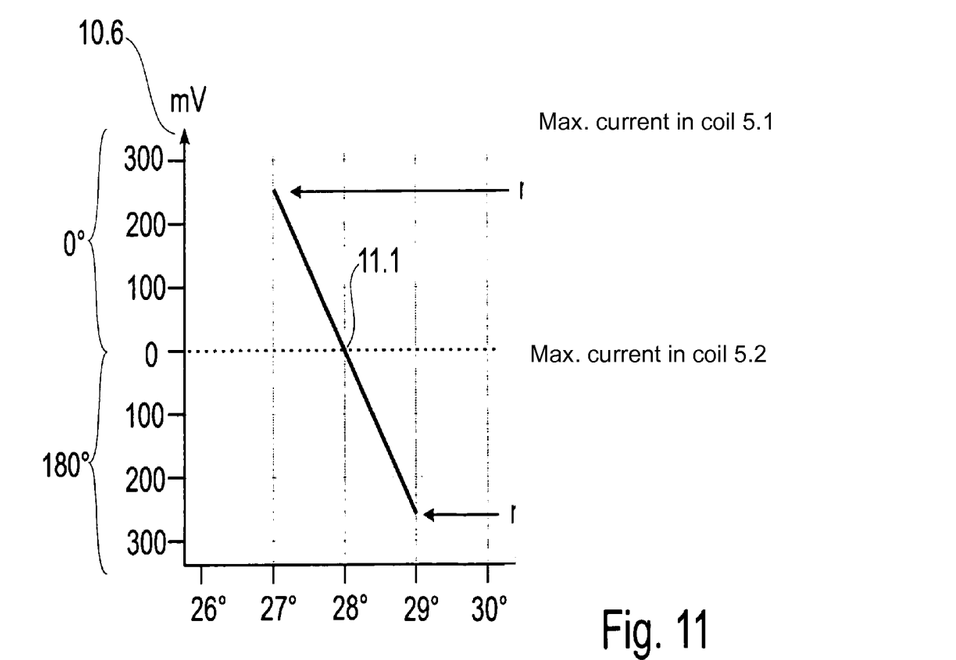
FIG. 11 shows the mode of operation of the arrangement according to FIG. 10 with reference to an output voltage in the receiving coil when the supply of current is displaced from one transmitting coil to the other.

FIG. 11 shows the mode of operation with reference to a possible output voltage 10.6 of the receiving coil 7.1 when the current supply is shifted from the coil 5.1 to the coil 5.7. In this case, the transmitting coil 5.1 is to be arranged at 27° and the transmitting coil 5.7 at 29°. If only the transmitting coil 5.1 is supplied with current, there is an output voltage of for example 250 mV with the same phase as the transmitting polarity. Regulating the current of the transmitting coil 5.1 to give smaller values and the current of the transmitting coil 5.7 to give larger values changes the output voltage 10.6 until the point 11.1 is reached, or in other words the transmitted magnetic fields are cancelled in the receiving coil 7.1. The output signal 10.6 becomes a zero signal. All the further measures which are taken for continuous regulation of the transmitting currents in order to continuously maintain a zero signal are described in detail in WO 2010/084000 A1 and WO 2010/133328 A1.

Figure 12:
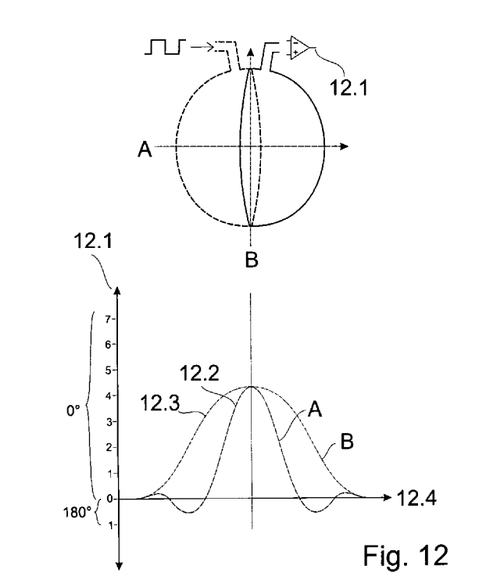
FIGS. 12 and 13 show the detection sensitivity of a coil arrangement operating by the classic "double D" principle and a coil arrangement according to the invention.
Figure 13:
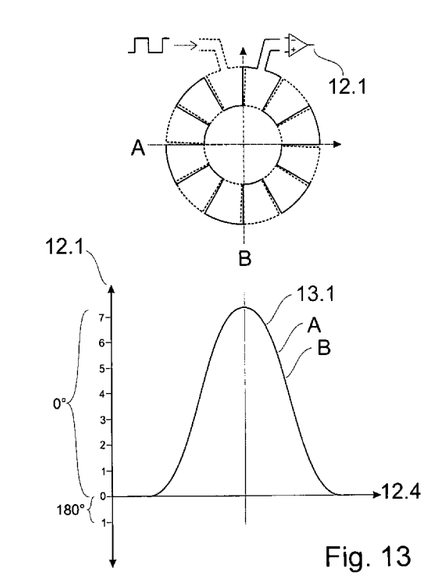

A further advantage of the coil arrangement described here, whether one or two transmitting coils are used, is illustrated in FIG. 12 and FIG. 13. In a test circuit, coils having the same number of windings (20 in each case), the same diameter (120 mm) and the same transmitting currents were used. FIG. 12 shows the coil arrangement using the classic "double D" principle, and FIG. 13 shows the novel coil arrangement with meandering coil.

A metal object (Cu, D=30 mm×5 mm) at a spacing of 100 mm was moved over the two coil arrangements in the direction A and B, and the output voltages 12.1 that occurred were measured. The graph of the voltage is plotted over the distance of travel 12.4. Different curves 12.2 and 12.3 of the output voltage 12.1 were produced in the two directions of movement A and B. The clear difference shows that the double D coil system in FIG. 12 has no rotationally symmetrical sensitivity. With the double D arrangement in FIG. 12, a reversal of polarity occurs in the direction of movement A. Significantly, this is particularly pronounced in the region near the coil, or in other words at a spacing from the coil of less than, for example, a quarter of the coil diameter, and may easily result in measurement errors in inductive measuring systems.

The coil system according to the invention in FIG. 13 behaves entirely differently. First of all, it displays significantly higher sensitivity. Further, the two curves 13.1 of the output voltage, in the two directions of movement A and B, are congruent. Thus, the coil system has an almost rotationally symmetrical sensitivity. "Almost" indicates that the more meandering loop portions are arranged on the coil periphery, the more rotationally symmetrical the sensitivity. In practice, for example, 6-8 meandering loop portions have proved useful for an entirely sufficient level of rotational symmetry. The near-field effects seen in the double D arrangement do not occur.

Figure 14:
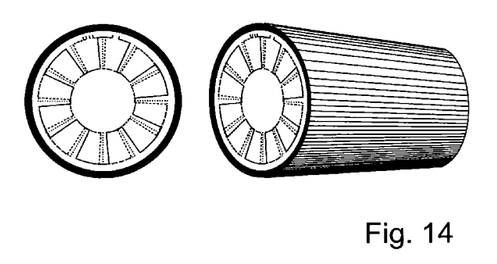
FIG. 14 shows a coil system incorporated into a metal surround.

Further, the meandering coil system has more insensitivity in the external region, which is an advantage for example if the coil system is accommodated in a tubular metal housing, as is conventional in the case of proximity sensors for automation engineering. In this arrangement, shown by FIG. 14, a suitable choice of coil angle 8.3 may allow the metal surround of the coil system to be screened out. Suitable angles that have proved useful in practice are offset angles in the region of ±2°.

Figure 15:
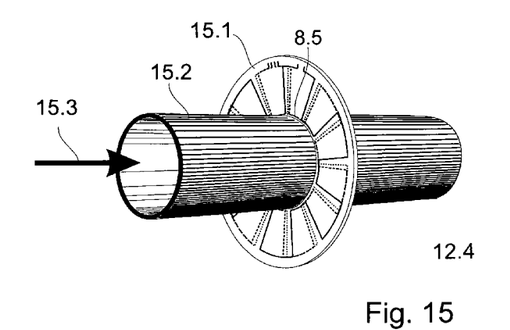
FIG. 15 shows the coil arrangement according to the invention with a central opening for a pipeline.

A further crucial advantage is shown by FIG. 15. The coil system 15.1 provides the possibility of a relatively large opening 8.5. Thus, a non-metallic or at least thin-walled metallic pipeline or similar may be guided through the coil arrangement. In this way, it is possible for example for abraded metal particles in a flowing liquid 15.3, for example hydraulic oil, to be detected with a high level of sensitivity.

The coils 5.1, 7.1 may be constructed appropriately and individually, and supplied to the sensor for manufacture.

It will be appreciated that this description may be subjected to a vast range of different modifications, changes and adaptations which are within the scope of equivalents to the attached claims.

The invention claimed is:

1. A sensor for locating metal objects, comprising:
   coils or coil parts that form at least one transmitting coil and at least one receiving coil, which are inductively coupled to one another and are arranged to partly overlap for a purpose of decoupling interaction, wherein a cancellation of the interaction may be achieved,
   a sensor electronics unit for supplying current to the transmitting coil and for analyzing a receiving signal from the receiving coil, and
   at least one regulated current source in which a control value for regulating an amplitude of current is supplied to the transmitting coil,
   wherein the transmitting coil and the receiving coil have a substantially identical coil shape and are rotated and/or offset in relation to one another, wherein a plurality of symmetrically arranged overlap regions are formed,
   wherein the substantially identical coil shape has loop portions that are meandering and arranged along a periphery of the coil or coil parts, wherein the loop portions have sections, which are arranged to have differing radial spacings from a centre point of the coil, and are connected alternately to one another to form an electrical conductor.

2. A sensor according to claim 1, wherein the overlap regions are arranged to have point symmetry in relation to the centre of the coils.

3. A sensor according to claim 1, wherein the coil or coil parts are planar and wherein the loop portions are each part of a winding of the coil or coil part.

4. A sensor according to claim 1, wherein the coil is circular and has n loop portions, wherein the loop portions of the transmitting coil and the receiving coil are arranged rotated about an angle of approximately $360°/(n*2)$.

5. A sensor according to claim 1, wherein the loop portions have circular sections at the differing radial spacings and are connected alternately to one another, by way of radially arranged sections, to form the electrical conductor.

6. A sensor according to claim 1, wherein a plurality of transmitting coils and at least one receiving coil are provided.

7. A sensor according to claim 1, wherein field lines of a field that is inverted in relation to field lines caused by a supply of current to the transmitting coil are formed within inwardly open loop portions of the receiving coil, while a field that acts in the same direction as field lines of the transmitting coil is formed in an interior of the receiving coil.

8. A sensor according to claim 1, wherein the periphery of the transmitting coil is approximately almost congruent with the periphery of the receiving coil.

9. A sensor according to claim 1, wherein a comparator is provided for comparing current signals that are associated with the transmitting coil in order to determine the control value, which continuously regulates the amplitude such that amplitudes of voltage signals at inputs of the comparator are of the same size, or that there is no difference in the voltage signals at the inputs of the comparator from both clock portions of a clock cycle.

* * * * *